United States Patent [19]

Chambers et al.

[11] Patent Number: 4,766,373
[45] Date of Patent: * Aug. 23, 1988

[54] METHOD AND APPARATUS FOR REAL-TIME, ON-LINE MONITORING OF WEAR IN MACHINERY

[75] Inventors: Keith W. Chambers, Pinawa; Clinton A. Waggoner, Victoria, both of Canada

[73] Assignee: Her Majesty the Queen in right of Canada, as represented by the Minister of National Defence, Canada

[*] Notice: The portion of the term of this patent subsequent to Mar. 17, 2004 has been disclaimed.

[21] Appl. No.: 16,791

[22] Filed: Feb. 20, 1987

Related U.S. Application Data

[63] Continuation of Ser. No. 593,653, Mar. 26, 1984, Pat. No. 4,651,091.

[30] Foreign Application Priority Data

Oct. 17, 1983 [CA] Canada .................................. 439146

[51] Int. Cl.$^4$ ..................... G01N 27/74; G01R 33/12; G01F 1/708; G01P 5/18
[52] U.S. Cl. .................................... 324/204; 324/227; 73/861.05
[58] Field of Search ................. 324/204, 227; 340/631; 73/861.05, 861.11, 64

[56] References Cited

U.S. PATENT DOCUMENTS 3,748,576 7/1973 Sigournay ........................... 340/631

OTHER PUBLICATIONS

Waggoner, "Problems in Bearings and Lubrication", AGARD paper from Conference Proceedings #323, 1982, pp. 2-1-2-21.
Jones, "Condition Monitoring '84", Proceedings by an International Conference on Condition Monitoring held at University College of Swansea, 4/1984, pp. 637-669.
Arneson et al., "Probe for Determining the Concentration of Ferromagnetic Particles in Water at High Temperatures", 1981, Power Industry Research, pp. 87-90.

Primary Examiner—Reinhard J. Eisenzopf
Assistant Examiner—Walter E. Snow
Attorney, Agent, or Firm—Stevens, Davis, Miller & Mosher

[57] ABSTRACT

The specification describes a method and an apparatus for detecting and quantitatively assessing wear of a machine having ferromagnetic components subjected to wear during operation resulting in the production of ferromagnetic particulate wear debris, and a lubrication system utilizing a lubricating fluid, in which the wear debris becomes entrained, for lubricating the components. The method comprises the steps of passing a sample stream of the lubricating fluid at a predetermined rate of flow axially through the core of an inductance coil of a sample oscillator for producing a time varying signal which deviates from a predetermined value in proportion to the mass of ferromagnetic material contained in the fluid passing through the core, monitoring the rate of change of signal and activating an indicator when the rate of change of the signal exceeds a predetermined level.

23 Claims, 3 Drawing Sheets

METHOD AND APPARATUS FOR REAL-TIME, ON-LINE MONITORING OF WEAR IN MACHINERY

This is a continuation application under 37 CFR §1.60 of prior application Ser. No. 593,653 filed Mar. 26, 1984, now U.S. Pat. No. 4,651,091.

The present invention relates to a method and apparatus for monitoring wear in machinery on a real time basis and providing a signal when an increase in the rate of wear is detected.

BACKGROUND OF THE INVENTION

It is highly desirable in some situations to monitor the degree of wear of machinery so as to not only maximize human safety by forestalling failure but also minimize downtime and its associated expense and inconvenience.

It is well known that most industrial and propulsion machinery utilize ferromagnetic components which, when subjected to wear during operation, produce ferromagnetic particulate wear debris which becomes entrained in the machinery lubricating fluid and that as components in the machinery age both the concentration and size of wear debris particles increase. These concepts form the basis of tests which have been developed for monitoring the degree of wear in machinery. A well known method of wear detection by the monitoring of wear debris in oil samples periodically removed from machinery is known as the "Spectrometric Oil Analysis Program" (SOAP). Another method involves the installation of easily removable magnetic plugs in the equipment. The plugs attract and accumulate ferrous wear debris produced during the course of operation of the machinery. The plugs are removed periodically and examined for wear debris accumulation.

The principal limitation of these and other known wear debris detection methods and apparatus is that they are incapable of sensing or quantitatively monitoring wear in machinery on a real time basis. In most cases, the machine must be shut down and samples must be taken and analysed before an indication of the condition of the machine can be obtained.

SUMMARY OF THE INVENTION

The present invention seeks to provide a method and an apparatus which, generally, overcomes the disadvantages the above referenced methods and, more specifically, continuously or substantially continuously monitors the concentration of suspended ferromagnetic particulate material in the lubrication circuits of machinery and provides a signal of impending failure.

It has been found that it is possible to monitor the concentration and the concentration ratio of coarse to fine particles of ferromagnetic wear debris produced by ferromagnetic components of a machine during operation of machinery by passing a sample stream of the lubricating fluid of the machine axially through the inductance coil of an oscillator circuit and monitoring the change of the frequency of the output signal of the oscillator. I is known that the inductance of an inductor is directly related to the permeability of the core of the inductance coil and that the frequency of the signal output by an oscillator is related to the inductance of the coil and, hence, to the permeability of the core of the coil. The mass or concentration of ferromagnetic material in the core of the inductance coil affects the permeability of the core and therefore the frequency of the oscillator output signal. Thus, a change in the mass or concentration of ferromagnetic material results in a corresponding change in the frequency of the oscillator output. The frequency of the output signal can accordingly be converted to a signal representative of the mass or concentration of ferromagnetic material within the core and a change in the frequency can be converted into a signal representative of the change of the concentration of the ferromagnetic material passing through the core.

In accordance with one aspect of the invention, there is provided a method of monitoring the wear of a machine having ferromagnetic components subjected to wear during operation resulting in the production of ferromagnetic particulate material, the machine having a lubrication system utilizing a lubricating fluid, in which the material becomes entrained, for lubricating the components. The method comprises the steps of passing a sample stream of the lubricating fluid at a predetermined rate of flow axially through the core of an inductance coil of a sample oscillator for producing a time-varying signal which deviates from a predetermined value in proportion to the mass of the ferromagnetic material in the fluid passing through the core, monitoring the rate of change of the signal, and activating an indicator when the rate of change of the signal exceeds a predetermined level.

In accordance with another aspect of the invention, there is provided a wear detector for a device having ferromagnetic components subjected to wear during operation resulting in the production of ferromagnetic particulate material, the device having a lubrication system utilizing a lubricating fluid, in which the material becomes entrained, for lubricating the ferromagnetic components. The detector comprises means defining a fluid flow passage having one end adapted to be connected to the device for taking a sample of the lubricating fluid from the device and and another end adapted to be connected to the device for returning the sample to the device.

The passage has a portion formed of non-ferromagnetic electric insulator material and the induction coil of an oscillator is disposed about this portion of the passage. The oscillator produces a time-varying signal which deviates from a predetermined value in proportion to the mass of ferromagnetic particulate material in the fluid stream passing through the core. An electrical circuit monitors the rate of change of the signal and produces an output signal when the rate of change of the signal exceeds a predetermined value. An indicator is responsive to the output signal for providing an indication of a wear condition.

BRIEF DESCRIPTION OF THE DRAWINGS

These and other features of the invention are described in greater detail in the following description in which reference is made to the appended drawings, wherein.

DETAILED DESCRIPTION OF A PREFERRED EMBODIMENT

Figure 1:
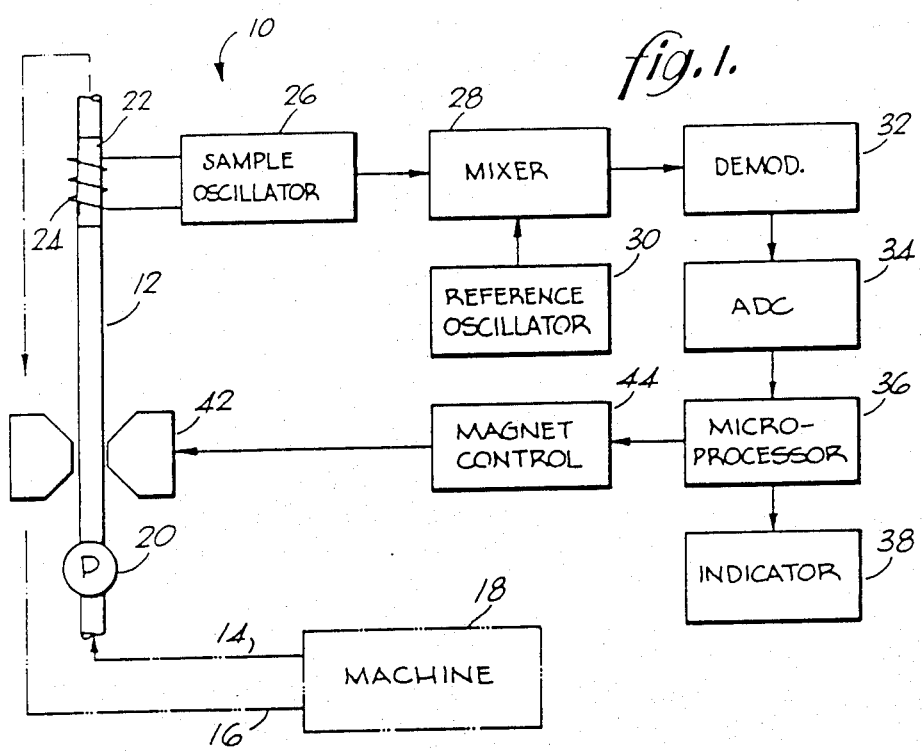
FIG. 1 is a block diagram of one embodiment of the present invention.

The method of the present invention generally involves passing a sample stream of the lubrication fluid of a machine axially through the core of the inductance coil of an oscillator, monitoring the rate of change of the output of the oscillator and activating an indicator when the rate of change of the output exceeds a predetermined acceptable level. The method is based on the fact that particle size and wear debris concentration increase as components of a machine age in terms of their operating life. The method is also based on the fact that the frequency of the output signal of an oscillator is directly related to the permeability of the inductance coil of the oscillator and that the permeability, in turn, is related to the mass of ferromagnetic material present within the core.

Generally, the mean particle size and concentration of particulate material wear debris produced by a component remain relatively constant during a major portion of the life of the component. Thus, the output of the oscillator would similarly remain relatively constant. In other words, the rate of change of the output of the oscillator will be relatively small. However, as the component approaches and reaches a critical age, the wear rate increases dramatically and, thus, so does the mean particle size and concentration of the particulate material. The increased wear rate will result in a change in the output of the oscillator and, more particularly, an increase in the rate of change of the oscillator output. A rate of change which exceeds a predetermined level, which can be determined experimentally for any given machine, is indicative of imminent failure of the component.

The method can be conducted on a continuous basis provided the concentration is sufficiently large to be detected by the oscillator. If the concentration is too small to be detected on a continuous basis, it is necessary to artificially increase the concentration by filtering or accumulating ferromagnetic wear debris upstream of the oscillator for a period of time, releasing the accumulated or trapped wear debris into the fluid stream and then monitoring the oscillator output or peak during the interval of time in which the accumulation of wear debris passes through the core of the oscillator. If the device which is adapted to carry out the method is arranged to monitor only the rate of change of concentration and not determine the actual concentration, no change of the device is necessitated by a conversion from a continuous to an intermittent mode.

As explained more fully later, the preferred method of accumulating ferromagnetic wear debris is to use a magnet adjacent the lubrication fluid flow pipe upstream of the oscillator and activating and deactivating the magnet at predetermined timed intervals. Thus, when the magnet is activated, ferromagnetic wear debris is attracted to and held against the interior surface of the flow pipe adjacent the magnet. The magnet may be an electromagnet which is activated by passing a current of a predetermined magnitude through its windings or a natural magnet which is deactivated by means of a suitable magnetic field.

It will be appreciated that, when operating in the intermittent mode, the rate of flow of the lubricating fluid through the core of the inductance coil must be maintained substantially constant or compensation for changing flow rate must be made when interpreting the output of the oscillator in order to obtain an accurate representation of the concentration or the rate of change of concentration of wear debris in the fluid. If the flow rate is increased, the mass of particulate material flowing through the core per unit time will increase and this will be reflected by an output which corresponds to a concentration which is higher than the actual concentration of the wear debris in the fluid. Conversely, if the flow rate is decreased, the mass of particulate material flowing through the core per unit time will decrease correspondingly and this will be reflected by an output which corresponds to a concentration which is lower than the actual concentration of the wear debris in the fluid.

The method by which particles of different sizes are detected is an extension of the intermittent detection method. This method involves accumulating ferromagnetic wear debris at two separate trapping sites, one employing a high and the other a low trapping current, in the fluid stream upstream of the coil. After an appropriate trapping interval, the accumulations are released into the fluid stream in predetermined time relation. If the accumulation sites are sufficiently separated, the accumulations may be released simultaneously. However, inasmuch as it is preferred to maintain the accumulation sites as close to the core as possible, the distal accumulation is released after an appropriate time delay following release of the accumulation at the proximal location.

The proportion of coarse to fine particles which accumulate at a trap varies with the trapping current: this enables the concentration ratio of coarse to fine particles and, hence, a wear severity index to be calculated from separate peak integrals corresponding to material released from each trap.

The method involves, therefore, determining the ratio of the concentration of fine ferromagnetic particulate material to the concentration of coarse ferromagnetic particulate material, determining the rate of change of the ratio and activating an indicator in the event that the rate of change of the ratio exceeds a preselected value. The ratio will be referred to hereinafter as the "wear severity index".

A single trapping magnet energized alternately at low and high trapping currents can also be used to generate wear severity indices but only at half the frequency.

The just described method can also be used to monitor the flow rate of the fluid through the core. This aspect of the method involves detecting the peak signal produced in response to each of the two accumulations flowing through the core, determining the time interval between the peaks and, after subtraction therefrom of the time delay, if any, between releases, dividing that interval into the volume of fluid contained between the two accumulation sites. Since the volume of fluid between the two accumulation sites remains constant, the time interval between the peaks is inversely proportional to the actual flow rate. Thus, the time interval can be converted directly to a flow rate by dividing the time interval into an appropriate constant if a display of the actual flow is desired. As with the monitoring of the concentration and particle size, any change in the time interval between peaks is indicative of a change in the flow rate of the fluid.

FIG. 1 is a block diagram of a wear detector which is operable in accordance with the intermittent method described above. It is to be understood, however, that substantially the same apparatus, but without the particle accumulator, can be used in accordance with the continuous method described above if the concentration of the ferromagnetic particulate material in the fluid stream is sufficiently large to be readily detected on this basis.

The detector is generally designated by reference numeral 10 and includes a conduit 12 having one end 14 adapted to be connected to a machine 18, the wear rate of which is to be monitored, for taking a sample of lubricating fluid therefrom and another end 16 adapted to be connected to the machine for returning the lubricating fluid thereto. A pump 20 is provided for maintaining a substantially constant rate of flow of lubricating fluid through conduit 12. A portion 22 of the conduit is formed of non-ferromagnetic electric insulator material and an inductance coil 24 of a sample oscillator 26 is wound about portion 22 of conduit 12 so that the lubricating fluid with ferromagnetic particulate wear debris entrained in it passes axially through the core of inductor 24.

The output of oscillator 26 as well as that of a crystal-controlled reference oscillator 30 are connected to a mixer 28. The mixer heterodynes the two signals to produce difference and sum frequencies which are applied to a demodulator 32. The output of the demodulator consists of the difference intermediate frequency (IF) which is digitized in an analog-to-digital converter 34 (ADC) and fed to a microprocessor 36. The microprocessor is arranged to energize an indicator 38 in a manner explained more fully later.

An electromagnet 42 is positioned upstream of inductance coil 24 and, under the control of microprocessor 36 via a magnet power supply 44, serves to attract and hold against the inside surface of conduit 12 ferromagnetic particulate material entrained in the lubricating fluid during predetermined time intervals.

Sample oscillator 26 and reference oscillator 30 are radio frequency (R.F.) oscillators with the former arranged to produce an output signal having a steady state frequency of 29.95 MHz and the latter arranged to produce an output signal at a frequency of 30 MHz. Thus, the steady state output of mixer 28 is a time-varying signal at an intermediate frequency of about 50 kHz.

The trapping interval, i.e., the interval of time within which the magnet is energized, will depend on a number of factors such as, for example, the flow rate, the size and concentration of particulate material and so forth. However, it has been determined that for a particulate material concentration in the range of 2 to 25 mg/Kg and higher, a flow rate of 1 liter/minute and a mean particle size less than 5 $\mu$m, a trapping time of 300 seconds (depending on rate of wear) is adequate in terms of detector sensitivity. It has been found that an ON/OFF duty cycle of 300 seconds ON and 30 seconds OFF provides adequate results for wear debris from propulsion engines, for example.

Upon de-energization of the magnet, the microprocessor begins to store the output of ADC 34 and continues to do so until the output has reached a steady state value. It has been determined that a detection period of 2.5 seconds is sufficient under the conditions described above. The microprocessor then processes the data in a manner which depends upon the nature and sophistication of output desired. At one extreme, it may be desired to provide a device which simply activates an indicator 38, such as a light or a buzzer, when the rate of change of the output exceeds the average rate of change of preceding samples by a predetermined amount. This may be achieved by integrating the transient portion of the output over the 2.5 second period, subtracting the result from the previous sample and comparing the result against similar data obtained in an appropriate number of previous samplings. At the other extreme, the the microprocessor may convert the integrated signal to a signal representative of the actual concentration of ferromagnetic particulate material in the fluid and display the actual concentration on an appropriate display. In yet another configuration, the microprocessor computes wear severity indices using data obtained from the release of accumulations at two different trapping currents as indicated earlier and described more fully hereinbelow.

Figure 2:
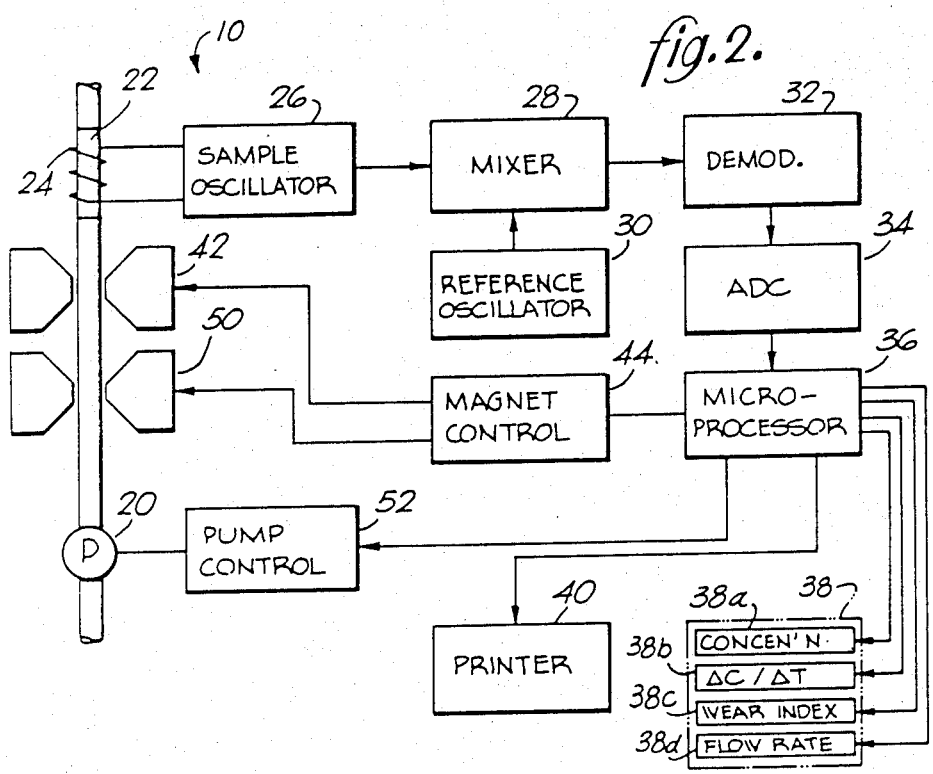
FIG. 2 is a block diagram of another embodiment of the invention.

The apparatus of FIG. 2 is arranged to calculate and display the actual concentration and the rate of change of concentration of the ferromagnetic particulate material entrained in the fluid flowing through conduit 12, a "wear severity index", the actual rate of flow of fluid through the conduit, and control the flow rate so as to maintain it within predetermined limits. As will become clear, the apparatus may also desirably include audible and/or visual indicators which are activated whenever the concentration, rate of change of concentration and/or wear severity index exceed predetermined levels and the flow rate deviates beyond its predetermined limits.

As with FIG. 1, the embodiment of FIG. 2 includes an inductance coil 24 of a sample oscillator 26, a reference oscillator 30, a mixer 28, a demodulator 32, an ADC 34, a microprocessor 36, a magnet control 44 and a proximate electromagnet 42. The apparatus of FIG. 2 additionally includes a distal electromagnetic 50 controlled by microprocessor 36 via magnet control 44 and a pump control circuit 52 responsive to microprocessor 36. As shown, distal electromagnet 50 is disposed upstream of proximal electromagnet 42.

The purpose of the two electromagnets is to obtain an indication of the ratio or proportion of coarse to fine particles of ferromagnetic material entrained within the fluid flowing through conduit 12. Since coarse particles are more readily trapped than fine particles, the two electromagnets are energized at different current levels. The particles accumulated at the trap energized at the lower current level will be comprised of coarser particles than the particles accumulated at the trap energized at a high current level.

Thus, under the control of microprocessor 36 and magnet control 44, distal magnet 50 is energized for a trapping interval of about 300 seconds at a low current level so as to accumulate coarser particles while proximal magnet 42 is energized for a similar trapping interval at a high current level so as to accumulate thereat fine particles. At the conclusion of the trapping intervals, the magnets are de-energized and the material accumulated at each trap is thus released into the fluid stream. The flow of the two accumulations through the inductance coil results in two IF excursions or peaks which are registered by sample oscillator 26 as previously explained. The first peak represents the material trapped at high current while the second peak represents the material trapped at low current. The magnets remain de-energized for a period of about 30 seconds and then the cycle is repeated. So as to permit the output of the sample oscillator to reach steady state after passage of the first accumulation through the inductance core, the distal electromagnet should be de-energized only after an appropriate time delay following de-energization of magnet 42. An appropriate delay would be 2.5 to 3 seconds.

The microprocessor uses the two resultant peak integrals to calculate the concentrations of the coarse and fine particles and the concentration ratio for coarse and fine particles. The latter is the wear severity index. The results are displayed on indicator 38a and 38c. The rates of change of the concentrations are also determined and displayed on indicator 38b.

The actual rate of flow of the fluid through conduit 12 is determined by detecting the time interval between the peak signal maxima produced in response to the flow of the two accumulations through the inductance coil, subtracting the time delay, if any, from the interval and dividing the resulting time interval into the volume of fluid between the two magnets. Since the volume between the two magnets remains constant, the flow rate can be obtained simply by dividing the time interval into an appropriate constant. The actual flow rate is displayed on an LED 38d. Once the flow rate has been determined, the microprocessor compares the actual flow against the desired flow rate, one litre per minute for example, and if the flow rate is found to be outside of predetermined limits, the microprocessor provides an appropriate signal to pump control circuit 52 which, in turn, adjusts the pump speed. Alternatively, the value of the peak integral can be normalized to a specific flow rate since the manner in which trapping and peak integral vary with flow rate can be readily determined.

The apparatus may also be used to detect the filtration efficiency of lubrication systems equipped with a bypass valve inasmuch as, for a constant rate of wear, a marked increase in the concentration of wear debris in the lubricating fluid is an indication of a clogged filter. Similarly, a blockage in the system can be detected by a sudden decrease in the flow rate. If desired, the outputs of microprocessor 36 may be fed to a printer 40 in order to obtain hard copy documentation.

Figure 3:
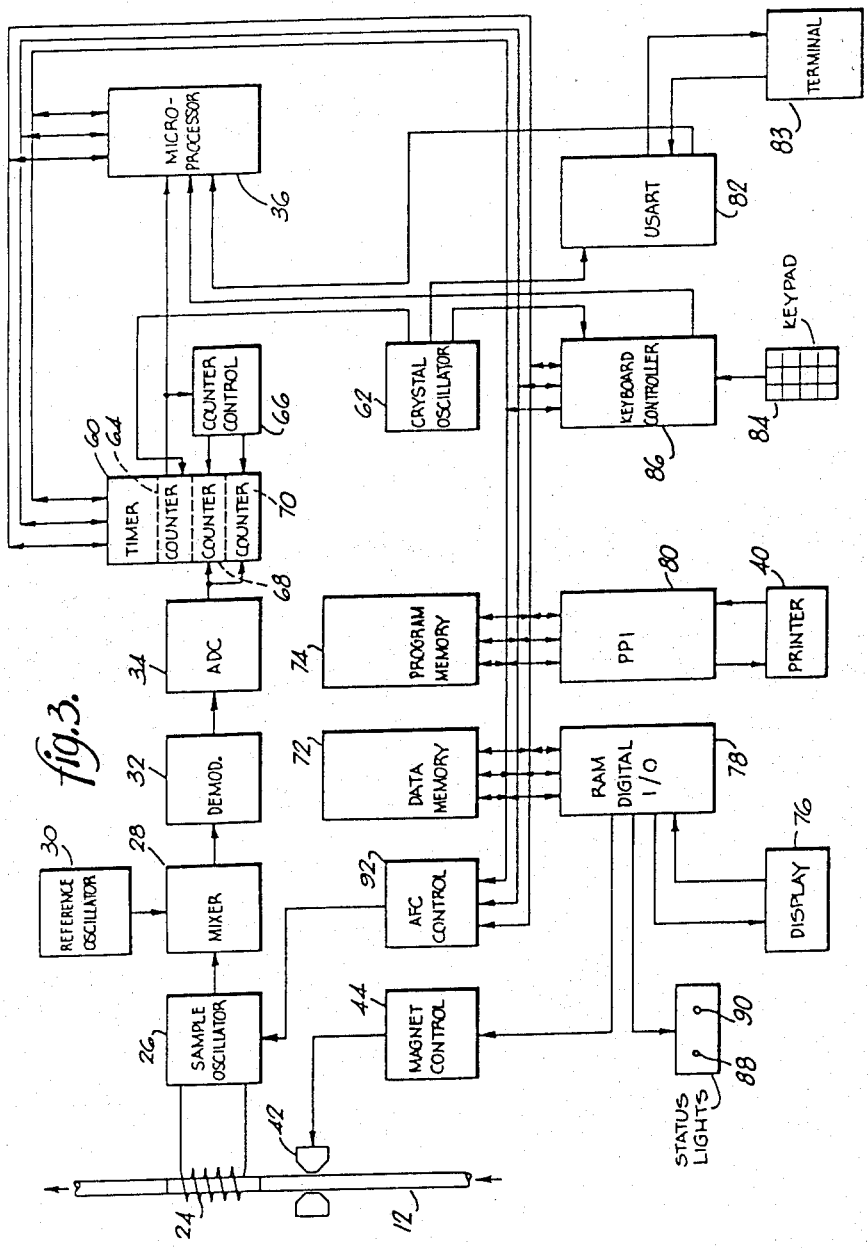
FIG. 3 is a block diagram electrical schematic of the electronic portion of a device constructed in accordance with the present invention.

FIG. 3 is a more detailed block diagram representation of the electrical circuit portion of the apparatus. The circuit may be used in conjunction with either of the two aforementioned embodiments.

As previously mentioned, the output of sample RF oscillator 26 and reference oscillator 30 are heterodyned in mixer 28. The sum and difference frequency output of mixer 28 is fed to demodulator 32 which, in turn, feeds the difference intermediate frequency (IF) signal to ADC 34. The output of ADC 34 is fed to one of two counters 68 and 70 which are part of a programmable interval timer 60 available as an integrated circuit part number 8253. When connected to ADC 34, counters 68 and 70 count the number of cycles of the digitized IF signal during a 50 ms period for storage in memory 72 under the control of the microprocessor as explained more fully below.

A crystal controlled oscillator 62 provides system timing. The output of oscillator 62 is connected to timer 64 of interval timer 60 which is programmed to provide a reference clock with a 50 ms period. This clock is used by the microprocessor, which operates under the control of programs stored in a programmable read only memory (PROM) 74, to provide all system timing intervals, such as the times at which the mganet(s) is energized and de-energized, with the times being multiples of the 50 ms period. The 50 ms clock is also fed to a control circuit 66 which controls digital counters 68 and 70. Thus, the digital frequency data output by ADC 34 is constantly fed to one of timers 68 and 70. When the microprocessor de-energizes the magnet, it immediately begins to read data from one of the counters. Every 50 ms, the currently active counter is stopped and the other counter is activated. The 50 ms clock signal informs the microprocessor that the switch of counters has taken place and it then reads the value from the idle counter, resets the counter and stores the data in a data memory 72. In this way, data is obtained first from one counter then from the other during the sampling period, which, as previously mentioned, is 2.5 seconds.

When all of the data from one peak has been stored in memory 72, the microprocessor initiates calculation of the various parameters, such as concentration, wear severity index, a running average concentration, current RF frequency baseline and flow rate as previously mentioned. Calculation results are output to a processor display 76 via a RAM input/output device 78 such as that available as part number 8155. Optionally, the results may be displayed on a printer 40 via programmable peripheral interface device 80 available as part number 8255 and on a remote data logger of computer 82 via a programmable communication interface device 84 available as part number 8251A. A microprocessor keypad 84 allows an operator to communicate with the microprocessor via a programmable interrupt controller 86 available as part number 8259. Thus, the keypad enables changing of system operational parameters, such as magnet cycle timing, constants used in calculating, which results are recorded, where results are printed, and so forth. Other processor features are controlled by the microprocessor to give the operator information relating the current state of the system and, for this purpose, two LED display lights 88 and 90 indicate magnet ON/OFF and magnet intensity, respectively.

When the calculations and reporting of results have been completed, the microprocessor will look at the collected data and determine the baseline RF input. This value is used to adjust the automatic frequency control (AFC) voltage with an appropriate signal transmitted to sample oscillator 26 via a digital-to-analog converter 92 so as to thereby compensate for long term drift caused by temperature changes in the RF section.

Figure 4:
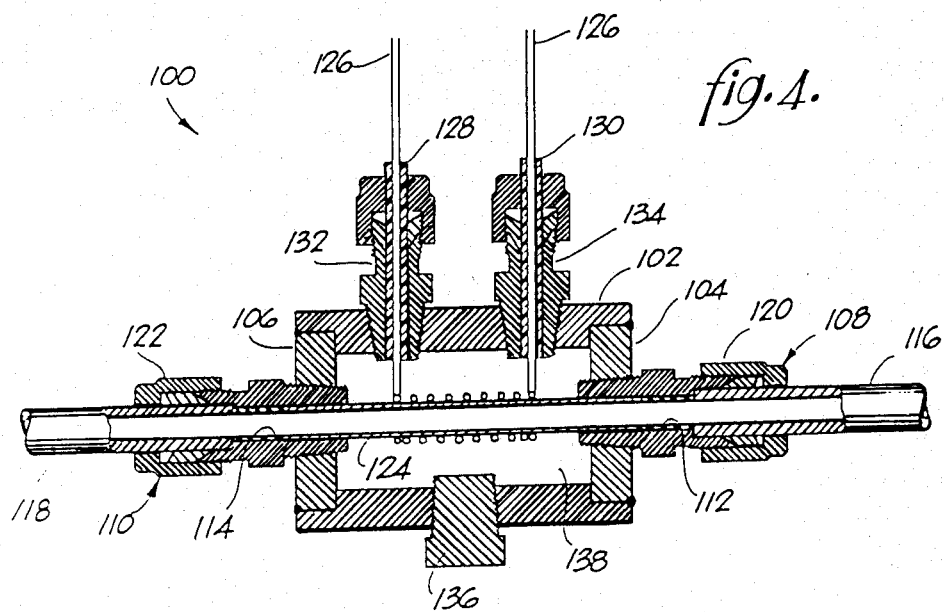
FIG. 4 is a longitudinal cross-sectional view of a transducer.

FIG. 4 is a longitudinal cross-sectional view taken through the inductive coil portion of the RF oscillator. This portion is hereinafter referred to as detector 100. The detector is formed with a cylindrical, tubular body 102 having disc-shaped end caps 104 and 106 welded to its opposed ends as shown. Swagelock connectors 108 and 110 are axially, threadedly connected to end caps 104 and 106, respectively, as shown. A non-magnetic tube, such as a pyrex tube, extends between bores 112 and 114 of connectors 108 and 110, respectively. A silicone rubber is used between the ends of the pyrex tube and the swagelock connectors in order to provide a primary oil seal therebetween. Stainless steel tubes 116 and 118 extend axially outwardly of connectors 108 and 110 and are secured thereto by means of swagelock male connectors 120 and 122, respectively. The pyrex tube, connectors and stainless tube are arranged so as to provide a uniform fluid passage 124.

An enamelled copper wire 126 is wound about the pyrex tube so as to form the inductance coil portion of the RF oscillator. It has been found that nine turns of the wire about the pyrex tube provides an adequate inductance coil for the purposes of the present invention. The wire extends through teflon sleeves 128 and 130 which, in turn, are received in swagelock connectors 132 and 134, respectively. The connectors are threadedly connected to cell body 102. A plug 136 is threaded into the cell body to serve as an inlet for admitting an epoxy filler into the internal cavity 138 defined by the cell body, end caps, and pyrex tube. The epoxy filler serves to support the pyrex tube.

Figure 5:
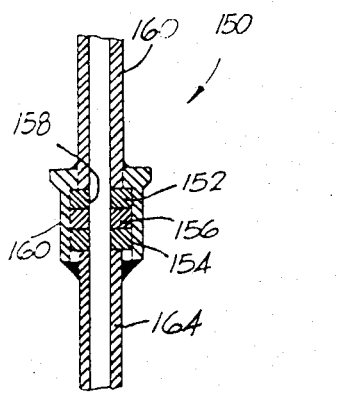
FIG. 5 is a longitudinal view of an electromagnet trap coupler.

FIG. 5 illustrates a trap coupler 150 for use as the core of the electromagnet. The trap coupler consists of three axially aligned and abutting stacked rings, the outer two of which, referenced by numerals 152 and 154, are formed of magnet iron while the inner ring 156 is formed of a non-ferromagnetic stainless steel, for example, type 316. The three rings are stacked together and are received in a sleeve 160; the stack is held in place by the sleeve 160 and tubes 162 and 164 which are welded into each end of the sleeve 160. The ring stack 152, 154 and 156 and tubes 162, 164 define a flow passage 158.

Figure 6:
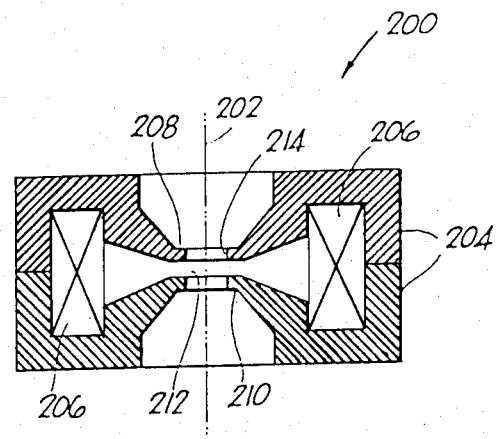
FIG. 6 is a longitudinal cross-sectional view of an electromagnet.

The magnetic field which is used to trap metal particles inside the trap coupler 150 is coupled into the soft iron rings 152 and 154 from the electromagnetic 200 which is shown in cross section in FIG. 6. The magnet is cylindrical, having an axis which is coincident with the flow passage axis 202. The magnet consists of two half yokes 204 which contain the magnet winding 206. When the winding is energized, a strong magnetic field is produced across the gap 212 between the ring-poles 208 and 210. The trap coupler fits snugly into the bore 214 in such a fashion that the soft iron ring 152, the stainless steel ring 156 and the soft iron ring 154 of the trap coupler are exactly aligned with the ring-pole 208, the gap 212 and the ring-pole 210 of the electromagnet, respectively. The magnetic field is thus coupled into the flow passage 158 of the trap coupler.

It will be understood that various modifications and alterations may be made to the above described invention without departing from the spirit of the following claims.

The embodiments of the invention in which an exclusive or property priviledge is claimed are defined as follows:

1. A method of monitoring the rate of wear of a machine having ferromagnetic components which wear during operation resulting in the production of ferromagnetic particulate material, said machine having a lubrication system utilizing a lubricating fluid, in which said material becomes entrained, for lubricating said components, said method comprising the steps of:
   passing a sample stream of said lubricating fluid at a uniform rate of flow axially through an inductance coil of an RF oscillator operating at a base frequenty arranged such that the frequency of the output signal of said oscillator deviates from said base frequency in proportion to the mass of the ferromagnetic material in the fluid passing through the coil;
   periodically accumulating ferromagnetic particulate material at a site in said sample stream upstream of said coil for a predetermined time interval;
   releasing material accumulated thereat at the conclusion of said interval; and
   integrating with respect to time the frequency transient in the oscillator output signal resulting from said the passage of said accumulated material through said inductance coil to provide a signal proportional to the concentration of ferromagnetic particulate material in said lubricating fluid; and
   comparing said proportional signal with a predetermined threshold to provide an indication of the rate of wear of said machine.

2. A method as defined in claim 1, further including the step of monitoring the rate of flow of said lubricating fluid through said coil and adjusting said flow rate so as to maintain it within predetermined limits.

3. A method as defined in claim 1, further including the steps of calculating the concentration of ferromagnetic particulate material in lubricating fluid flowing through said coil on the basis of the difference between the frequency of said output signal and said base frequency and activating an indicator when the calculated value exceeds a predetermined threshold level.

4. A method as defined in claim 1, further including the steps of determining the average value of said oscillator output signal over a predetermined time interval and activating an indicator when the value of the signal output by said oscillator exceeds said average value by a predetermined amount.

5. A method as defined in claim 1, further including the step of determining a wear severity index and activating an indicator when said index exceeds a predetermined value.

6. A method as defined in claim 2, said step of monitoring the rate of flow of said fluid including the steps of accumulating ferromagnetic particulate material in said stream at two separate sites upstream of said coil for equal predetermined intervals of time, releasing accumulated material at said sites into said stream in predetermined timed sequence, detecting the time interval between the arrival of said accumulations at said coil and converting said detected time into a flow rate.

7. A method as defined in claim 6, wherein said accumulations are released simultaneously.

8. A method as defined in claim 6, wherein the accumulation at a proximal site is released in advance of the accumulation at a distal site.

9. A method as defined in claim 5, wherein said step of determining a wear severity index includes the steps of determining the concentration of coarse and fine particles in said stream and determining the ratio one of said concentrations to the other of said concentrations.

10. A method as defined in claim 7, wherein said step of determining a wear severity index further includes accumulating both coarse and fine particles at a first predetermined site upstream of said coil for a predetermined time interval at a first trapping current, accumulating both coarse and fine particles at a second site spaced from said first site upstream of said coil for a predetermined time interval at a second trapping current and releasing the accumulations at said sites in predetermined timed sequence.

11. A method as defined in claim 9, wherein said step of determining a wear severity index further includes accumulating both coarse and fine particles at a single site upstream of said coil for a predetermined time interval at a first trapping current and releasing the accumulation, accumulating at the same site both coarse and fine particles for a predetermined time interval at a second trapping current and releasing the accumulation.

12. A method as defined in claim 1, said method further including the step of mixing said oscillator output signal with a reference signal having a reference frequency for producing a signal having both sum and difference frequencies and demodulating said signal to provide an IF output signal at the difference intermediate frequency.

13. A method as defined in claim 12, said integrating step including counting the number of cycles of said IF output signal during a second predetermined time interval subsequent to the conclusion of said time interval and within which said accumulated material passes through said coil, and converting the resultant count to signal representative of the concentration of ferromagnetic material in said fluid stream.

14. A real-time, on-line apparatus for monitoring the rate of wear of a machine having ferromagnetic components which wear during operation resulting in the production of ferromagnetic particulate material, said machine having a lubrication system utilizing a lubricating fluid, in which said material becomes entrained, for lubricating said ferromagnetic components, said apparatus comprising:
  means defining a fluid flow passage having one end adapted to be connected to said machine for taking a sample of said lubricating fluid from said machine and another end adapted to be connected to said machine for returning said sample to said machine, said passage having a portion thereof formed of nonmagnetic material;
  sensing means including an RF oscillator having an inductance coil disposed about said portion of said passage means, said oscillator being adapted to operate at a base RF frequency and produce an RF output signal, said coil being arranged such that the frequency of said RF output signal deviates from said base RF frequency in proportion to the mass of ferromagnetic particulate material entrained in the fluid passing through said coil;
  means for accumulating ferromagnetic material in said sample stream upstream of said inductance coil; and
  electrical circuit means for:
    (a) integrating with respect to time the frequency transient in said RF output signal resulting from the passage of said accumulated material through said coil to provide an integrated output signal;
    (b) comparing said integrated output signal against a predetermined threshold and providing a second output signal representative of the rate of wear of said machine; and
    (c) controlling said accumulating means so as to activate said accumulating means for predetermined timed intervals at predetermined increments of time whereby to accumulate ferromagnetic particulate material at said site and deactivate said accumulating means at the end of said intervals whereby to release any accumulation at said site into said fluid passage.

15. An apparatus as defined in claim 14, said means defining a fluid flow passage including a housing having an interior chamber, a non-ferromagnetic electric insulator means defining said fluid flow passage, said inductance coil being disposed within said chamber and wound about said insulator means within said housing, and means disposed within said housing for radially supporting said passage means along the length thereof.

16. An apparatus as defined in claim 14, said accumulating means including an electromagnet responsive to said electrical circuit means for accumulating and releasing said ferromagnetic particulate material.

17. An apparatus as defined in claim 16, said electromagnetic having a cylindrical tubular core of magnetic material defining a further portion of said passage and an electrical winding disposed about said core and electrically connected to said circuit means.

18. An apparatus as defined in claim 14, further including a reference oscillator for producing a time-varying signal having a nominal reference frequency, a mixer for combining said time-varying signals and for producing a signal having both sum and difference frequencies and demodulating said signal to provide an IF output signal having a difference intermediate frequency, said electrical circuit means being responsible to said IF output signal.

19. An apparatus as defined in claim 14, said electrical circuit means further including means for maintaining a constant rate of flow through said passage means.

20. An apparatus as defined in claim 14, said electrical circuit means further including means for monitoring the rate of flow of fluid through said passage and providing an indication of a change in said rate of flow.

21. An apparatus as defined in claim 14, said accumulating means being an electromagnet, said apparatus further including a second electromagnet for accumulating ferromagnetic particulate material in said passage, said second electromagnet being disposed upstream of said first mentioned electromagnet;
  said electrical circuit means being operable to control the electrical current flow through said electromagnets whereby one of said electromagnets may be operated at a first trapping current for accumulating fine ferromagnetic particulate material thereat and the other of said electromagnets may be operated at a second and different trapping current for accumulating coarser ferromagnetic particulate material thereat; and
  said electrical circuit means being further operable to deactivate said electromagnets in predetermined times relation and provide a signal proportional to the ratio of the concentration of fine and coarse ferromagnetic particulate material.

22. A method of monitoring the wear of a machine having ferromagnetic components subjected to wear during operation resulting in the production of ferromagnetic particulate material, said machine having a lubrication system utilizing a lubricating fluid, in which said material becomes entrained, for lubricating said components, said method comprising the steps of:
  passing a sample stream of said lubricating fluid at a predetermined rate of flow axially through an inductance coil of an RF oscillator operating at a base frequency arranged such that the frequency of the output signal of said oscillator deviates from said base frequency in proportion to the mass of the ferromagnetic material in the fluid passing through said core;
  periodically accumulating ferromagnetic particulate material at a site in said sample stream upstream of said coil for a predetermined time interval;
  releasing material accumulated thereat at the conclusion of said interval;
  detecting the change of the frequency of said output signal from said base frequency;

monitoring the rate of flow of said lubricating fluid through said core and adjusting said flow rate so as to maintain it within predetermined limits, said monitoring step including the steps of accumulating ferromagnetic particulate material in said stream at two separate sites upstream of said core for equal predetermined intervals of time, releasing accumulated material at said sites into said stream in predetermined timed sequence, detecting the time interval between the arrival of said accumulations at said core and converting said detected time into a flow rate.

23. An apparatus for monitoring the rate of wear of a machine having ferromagnetic components subjected to wear during operation resulting in the production of ferromagnetic particulate material, said machine having a lubrication system utilizing a lubrication fluid, in which said material becomes entrained, for lubricating said ferromagnetic components, said apparatus comprising:

means defining a fluid flow passage having one end adapted to be connected to said device for taking a sample of said lubrication fluid from said device and another end adapted to be connected to said device for returning said sample to said device, said passage having a portion thereof formed of non-magnetic material;

an RF oscillator having an induction coil disposed about said portion of said passage means, said oscillator being adapted to operate at a base RF frequency and product an RF output signal, said coil being arranged such that the frequency of said RF output signal deviates from said base RF frequency in proportion to the mass of ferromagnetic particulate material entrained in the fluid passing through said core;

means for accumulating ferromagnetic material in said sample stream upstream of said inductance coil;

electrical circuit means for monitoring the change of the frequency of said signal and producing an output signal when the change of the frequency of said signal exceeds a predetermined value and controlling said accumulating means whereby to activate said accumulating means for predetermined timed intervals at predetermined increments of time whereby to accumulate particulate at said site and to deactivate said accumulating means at the end of said intervals whereby to release any accumulation at said site into said fluid passage; and means responsive to said circuit means output signal for providing an indication of a wear condition;

means for monitoring the rate of flow of fluid through said passage and providing an indication of a change in said rate of flow, said means for monitoring the rate of flow of fluid through said passage including:

first means for accumulating ferromagnetic particulate material in said passage upstream of said coil;

second means for accumulating ferromagnetic particulate material in said passage upstream of said coil;

control means for activating and deactivating said first and second accumulating means;

means responsive to the output of said oscillator for detecting the peak position with respect to time thereof produced in response to accumulated material released by said accumulating means and flowing through said core;

timer means responsive to said peak positions for determining the time interval between the peak positions and producing a signal representative of said interval; and means responsive to said interval representative signal for producing a signal representative of the flow rate of said fluid in said passage.

* * * * *